United States Patent
Root et al.

(10) Patent No.: US 8,152,715 B2
(45) Date of Patent: Apr. 10, 2012

(54) ENDOSCOPE WITH INTERNAL LIGHT SOURCE AND POWER SUPPLY

(75) Inventors: Thomas V. Root, Beverly, MA (US);
Robb M. Gavalis, Bolton, MA (US);
Robert J. Krupa, Leominster, MA (US);
Anthony J. Parillo, Sherborn, MA (US);
William F. Laflash, Northbridge, MA (US); Aleksandra Levshina, Leominster, MA (US)

(73) Assignee: Optim, Incorporated, Sturbridge, MA (US)

( * ) Notice: Subject to any disclaimer, the term of this patent is extended or adjusted under 35 U.S.C. 154(b) by 1243 days.

(21) Appl. No.: 11/855,780

(22) Filed: Sep. 14, 2007

(65) Prior Publication Data
US 2009/0076328 A1    Mar. 19, 2009

(51) Int. Cl.
*A61B 1/06* (2006.01)
(52) U.S. Cl. ......... 600/131; 600/133; 600/159; 600/178
(58) Field of Classification Search ............... 600/131, 600/133, 178–180
See application file for complete search history.

(56) References Cited

U.S. PATENT DOCUMENTS

| | | |
|---|---|---|
| 3,111,230 A | 11/1963 | Pesenti |
| 3,299,731 A | 1/1967 | Russell, Jr. |
| 3,365,975 A | 1/1968 | Hathaway |
| 3,394,611 A | 7/1968 | Beurrier |
| 3,897,775 A | 8/1975 | Furihata |
| 3,938,402 A | 2/1976 | Citrin |
| 3,963,438 A | 6/1976 | Banez |
| 3,986,498 A | 10/1976 | Lewis |
| 4,078,555 A | 3/1978 | Takahashi |
| 4,101,197 A | 7/1978 | Kent et al. |
| 4,212,021 A | 7/1980 | Ono et al. |
| 4,385,344 A | 5/1983 | Gonser |
| 4,449,518 A | 5/1984 | Konomura et al. |
| 4,474,174 A | 10/1984 | Petruzzi |
| D277,505 S | 2/1985 | Kubokawa et al. |
| 4,534,208 A * | 8/1985 | Macin et al. .................. 73/49.3 |
| 4,617,915 A | 10/1986 | Arakawa |
| 4,739,128 A | 4/1988 | Grisham |
| 4,763,100 A | 8/1988 | Wood |
| 4,803,992 A | 2/1989 | Lemelson |
| 4,850,716 A | 7/1989 | Baker et al. |
| 4,862,872 A | 9/1989 | Yabe et al. |

(Continued)

FOREIGN PATENT DOCUMENTS
DE          20211713        11/2002
(Continued)

OTHER PUBLICATIONS

Non-Final Office Action dated Aug. 18, 2009 in co-pending U.S. Appl. No. 11/599,196, "Portable Endoscope," filed Nov. 14, 2006.

(Continued)

*Primary Examiner* — Matthew J Kasztejna
(74) *Attorney, Agent, or Firm* — Brian M. Dingman; Mirick, O'Connell, DeMallie & Lougee, LLP (57) ABSTRACT

The present invention provides an endoscope with a watertight and air-tight endoscope handle that in preferred embodiments contains in its interior a solid-state light source and a gas permeable and liquid impermeable sealed compartment holding a battery and an electronic circuit, where the sealed compartment is preferably transverse to the long axis of the endoscope handle, and, in certain embodiments, at least partially surrounded by a movable structure.

24 Claims, 7 Drawing Sheets

U.S. PATENT DOCUMENTS

| | | | |
|---|---|---|---|
| 4,911,148 A | 3/1990 | Sosnowski et al. | |
| 4,919,113 A | 4/1990 | Sakamoto et al. | |
| 4,947,828 A | 8/1990 | Carpenter et al. | |
| 4,974,607 A | 12/1990 | Miwa | |
| 4,998,926 A | 3/1991 | Alchas | |
| 5,050,449 A | 9/1991 | Falcou et al. | |
| D330,020 S | 10/1992 | Jung | |
| 5,183,031 A * | 2/1993 | Rossoff | 600/131 |
| D333,601 S | 3/1993 | Wingert | |
| 5,199,417 A | 4/1993 | Muller et al. | |
| D335,710 S | 5/1993 | Ainger, III | |
| 5,217,003 A | 6/1993 | Wilk | |
| 5,238,025 A | 8/1993 | Preston | |
| 5,290,279 A | 3/1994 | Bonati et al. | |
| 5,359,993 A | 11/1994 | Slater et al. | |
| 5,368,015 A | 11/1994 | Wilk | |
| 5,373,317 A | 12/1994 | Salvati et al. | |
| 5,408,991 A | 4/1995 | Iida | |
| D358,471 S | 5/1995 | Cope et al. | |
| 5,497,847 A | 3/1996 | Ota et al. | |
| 5,535,141 A | 7/1996 | Lussi | |
| 5,586,207 A | 12/1996 | Goodwin | |
| 5,588,950 A | 12/1996 | Sano et al. | |
| 5,609,561 A | 3/1997 | Uehara | |
| 5,630,783 A | 5/1997 | Steinberg | |
| 5,634,711 A | 6/1997 | Kennedy et al. | |
| 5,655,411 A | 8/1997 | Avitan et al. | |
| 5,680,492 A | 10/1997 | Hopler et al. | |
| 5,732,401 A | 3/1998 | Conway | |
| 5,733,242 A * | 3/1998 | Rayburn et al. | 600/120 |
| 5,830,121 A | 11/1998 | Enomoto et al. | |
| 5,846,183 A | 12/1998 | Chilcoat | |
| D410,286 S | 5/1999 | Tamirisa | |
| 5,920,054 A | 7/1999 | Uber, III | |
| 5,984,875 A | 11/1999 | Brune | |
| 6,004,263 A * | 12/1999 | Nakaichi et al. | 600/176 |
| 6,033,360 A | 3/2000 | Sano et al. | |
| 6,059,718 A | 5/2000 | Taniguchi et al. | |
| 6,092,722 A | 7/2000 | Heinrichs et al. | |
| 6,092,935 A | 7/2000 | Althaus et al. | |
| 6,106,457 A * | 8/2000 | Perkins et al. | 600/175 |
| 6,193,510 B1 | 2/2001 | Tsimerman | |
| 6,240,312 B1 | 5/2001 | Alfano et al. | |
| 6,260,994 B1 | 7/2001 | Matsumoto et al. | |
| 6,315,710 B1 | 11/2001 | Rovegno | |
| 6,318,887 B1 | 11/2001 | Matsumoto | |
| 6,331,156 B1 | 12/2001 | Haefele et al. | |
| 6,361,489 B1 * | 3/2002 | Tsai | 600/109 |
| 6,366,206 B1 | 4/2002 | Ishikawa et al. | |
| 6,436,032 B1 | 8/2002 | Eto et al. | |
| 6,438,302 B1 | 8/2002 | Utsui et al. | |
| 6,452,624 B1 | 9/2002 | Aloy | |
| 6,461,295 B2 | 10/2002 | Takada | |
| 6,485,684 B1 | 11/2002 | Mapson et al. | |
| D466,773 S | 12/2002 | Lin | |
| 6,554,765 B1 | 4/2003 | Yarush | |
| 6,652,453 B2 * | 11/2003 | Smith et al. | 600/188 |
| 6,679,835 B2 | 1/2004 | Moriyama | |
| 6,692,432 B1 * | 2/2004 | Yarush | 600/179 |
| 6,712,756 B1 | 3/2004 | Kura et al. | |
| 6,712,760 B2 | 3/2004 | Sano et al. | |
| 6,726,620 B2 | 4/2004 | Shibata et al. | |
| D495,413 S | 8/2004 | Perry | |
| 6,776,537 B2 | 8/2004 | Toyama | |
| 6,793,622 B2 | 9/2004 | Konomura et al. | |
| 6,814,932 B2 | 11/2004 | Hlebovy et al. | |
| 6,832,849 B2 | 12/2004 | Yoneda et al. | |
| 6,884,392 B2 | 4/2005 | Malkin et al. | |
| 6,918,693 B2 | 7/2005 | Ota et al. | |
| 6,921,920 B2 | 7/2005 | Kazakevich | |
| 6,932,599 B1 | 8/2005 | Hartung | |
| 7,063,663 B2 | 6/2006 | Kazakevich | |
| D533,662 S | 12/2006 | Nakajima et al. | |
| D533,939 S | 12/2006 | Root et al. | |
| 7,229,201 B2 | 6/2007 | Krupa et al. | |
| D581,052 S | 11/2008 | Root et al. | |
| 7,942,813 B2 * | 5/2011 | Mackin | 600/120 |
| 2001/0018551 A1 | 8/2001 | Komi | |
| 2001/0033807 A1 | 10/2001 | Lin et al. | |
| 2001/0041825 A1 | 11/2001 | Shibata et al. | |
| 2001/0056224 A1 | 12/2001 | Renner et al. | |
| 2002/0013510 A1 | 1/2002 | Moriyama | |
| 2002/0022769 A1 * | 2/2002 | Smith et al. | 600/188 |
| 2002/0103419 A1 | 8/2002 | Christopher | |
| 2002/0120181 A1 | 8/2002 | Irion | |
| 2002/0137987 A1 | 9/2002 | Watanabe et al. | |
| 2002/0188173 A1 | 12/2002 | Kobayashi | |
| 2003/0050534 A1 * | 3/2003 | Kazakevich | 600/178 |
| 2003/0109837 A1 | 6/2003 | McBride-Sakal | |
| 2003/0141507 A1 | 7/2003 | Krames et al. | |
| 2003/0149339 A1 | 8/2003 | Ishibiki | |
| 2003/0156430 A1 | 8/2003 | Oto et al. | |
| 2003/0231843 A1 | 12/2003 | Columbo et al. | |
| 2003/0235800 A1 | 12/2003 | Qadar | |
| 2004/0004846 A1 | 1/2004 | Steen et al. | |
| 2004/0024290 A1 | 2/2004 | Root et al. | |
| 2004/0041031 A1 | 3/2004 | Root et al. | |
| 2004/0049172 A1 | 3/2004 | Root et al. | |
| 2004/0052679 A1 | 3/2004 | Root et al. | |
| 2004/0059191 A1 | 3/2004 | Krupa et al. | |
| 2004/0133076 A1 | 7/2004 | Kobayashi et al. | |
| 2004/0186352 A1 * | 9/2004 | Roberts et al. | 600/200 |
| 2004/0225190 A1 | 11/2004 | Kimoto et al. | |
| 2004/0246744 A1 | 12/2004 | Krupa et al. | |
| 2005/0043591 A1 * | 2/2005 | Witte | 600/200 |
| 2005/0075539 A1 | 4/2005 | Schulz et al. | |
| 2005/0267329 A1 | 12/2005 | Konstorum et al. | |
| 2006/0015014 A1 | 1/2006 | Remijan et al. | |
| 2007/0153541 A1 | 7/2007 | Bennett et al. | |
| 2007/0225561 A1 * | 9/2007 | Watanabe et al. | 600/118 |
| 2007/0282167 A1 | 12/2007 | Barenboym et al. | |
| 2008/0114207 A1 | 5/2008 | Krupa et al. | |
| 2008/0132760 A1 | 6/2008 | Takeuchi | |

FOREIGN PATENT DOCUMENTS

| | | |
|---|---|---|
| JP | 5264871 | 10/1993 |
| JP | 5313045 | 11/1993 |
| JP | 8317897 | 12/1996 |
| JP | 03/135367 | 5/2003 |
| JP | 04/129720 | 4/2004 |
| WO | WO 01/95228 A1 | 12/2001 |
| WO | WO 02/19900 A1 | 3/2002 |
| WO | WO 02/071930 A1 | 9/2002 |
| WO | WO 02/017171 A1 | 7/2003 |
| WO | WO 03/079888 A2 | 10/2003 |
| WO | WO 2006/055949 A1 | 5/2006 |
| WO | WO 2006/066022 A2 | 6/2006 |
| WO | WO 2008/061106 | 5/2008 |

OTHER PUBLICATIONS

Final Office Action dated Apr. 27, 2010 in co-pending U.S. Appl. No. 11/599,196, "Portable Endoscope," filed Nov. 14, 2006.

Information Disclosure Statement dated Aug. 1, 2007 filed by Applicant in co-pending U.S. Appl. No. 11/599,196, "Portable Endoscope," filed Nov. 14, 2006.

Information Disclosure Statement dated Jun. 17, 2008 filed by Applicant in co-pending U.S. Appl. No. 11/599,196, "Portable Endoscope," filed Nov. 14, 2006.

Supplementary European Search Report and European Search Opinion, dated Sep. 27, 2010, in co-pending European application 08831174.1.

International Search Report in PCT/US2008/076211, Date of Mailing—Nov. 17, 2008.

* cited by examiner

ENDOSCOPE WITH INTERNAL LIGHT SOURCE AND POWER SUPPLY

BACKGROUND OF THE INVENTION

Endoscopes are commonly used to view within an actual or potential space inside a subject (e.g., a human, or animal) or manufactured structure (e.g., an engine or a pipe) while performing a therapeutic or diagnostic procedure. Typically, an endoscope has a control handle coupled to an elongated portion (e.g., a flexible elongated portion, a rigid elongated portion, a semi-rigid elongated portion). During use of the endoscope, the control handle remains outside the subject while the elongated portion is at least partially disposed inside the subject. Generally, the elongated portion has one or more optical components (e.g., one or more lenses, fiber optics, video imager) to illuminate and view the region inside the subject, and the control handle has one or more devices designed to control the optical components (e.g., to control light intensity, focus an image, display and image, digitize an image) and the position of the elongated portion in the subject.

Typically the light source, the light source power supply and other features and controls (such as irrigation and suction) are placed in a separate console that is connected to the endoscope handle by an umbilical cable that includes a light guide. Traditional light sources for endoscopic use are generally of two types: incandescent filament lamps and arc lamps. Both types of lamps are very inefficient in converting electrical power to light, and consequently produce large amounts of heat that must be dissipated. Because of the heat generated and the need for a bulky light source power supply, these light sources typically reside outside of the endoscope itself.

Figure 1:
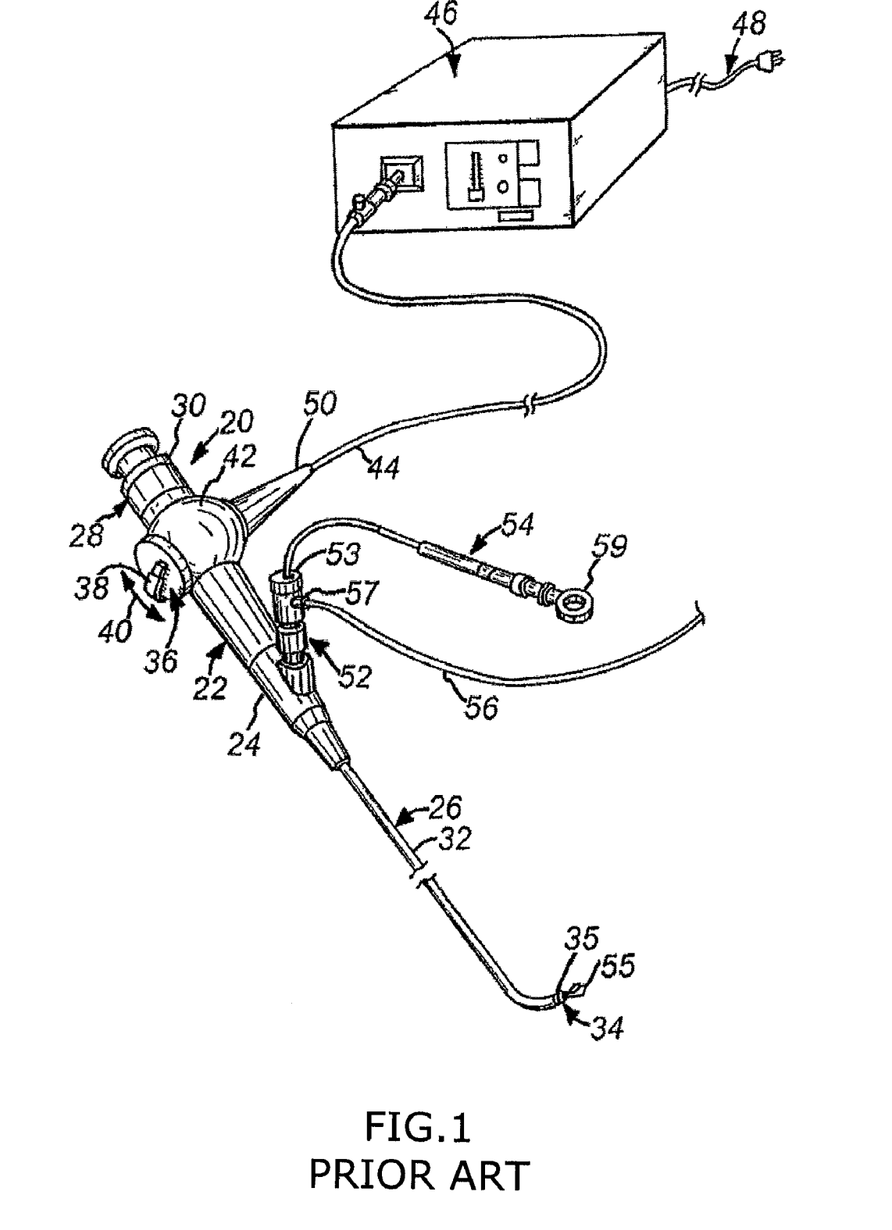
FIG. 1 is a perspective view of a prior art endoscope having a separate light source with an AC power incandescent lamp.

An illustrative endoscope according to the prior art is shown in FIG. 1, which is simplified from FIG. 1 of U.S. Pat. No. 5,630,783. The endoscope 20 includes a housing or handle 22 having an elongated distal portion 24 that supports a flexible tube 26. The handle 22 also includes an eyepiece 28 at the proximal end of the handle 22. The eyepiece 28 can include a focus ring 30. The tube 26 typically includes an outer covering 32 constructed from a low-friction polymer. The distal end 34 of the tube 26 typically includes a polished metal end cap 35 having a plurality of exit ports. The handle 22 includes a movable steering control 36 with a steering lever or knob 38. The steering lever 38 moves (arrow 40) proximally and distally along the handle to control a pair of steering cables (not shown) within the tube 26. The steering cables enable the distal end 34 of the tube 26 to bend. The steering control 36 is mounted on an enlarged ball 42 located between the proximal end and the distal end of the handle 22.

A connector 50 links the ball 42 with a fiber optic light source cable 44 that communicates with a light source 46 according to the prior art. The light source 46 is, typically, a variable-intensity incandescent or arc lamp that draws power from a conventional AC power source via an electrical cord 48. An associated internal illumination light guide (not shown) is optically linked within the ball 42 of the handle 22 with the light source cable 44. The internal illumination light guide extends through the distal end 24 of the handle 22 and passes along the full length of the tube 26, and is exposed at the distal end 34 of the tube 26 to provide light at the distal end. According to the prior art, an irrigation/instrument assembly 52 or other fitting is optionally provided at the distal end 24 of the handle 22. The assembly 52 interconnects with an internal tube (not shown) that exits at the distal end 34 of the tube 26. The assembly 52 includes an instrument port 53 that provides a conduit for guiding an actuating mechanism of an instrument such as the grasper 55 located at the tube's distal end 34. A remote plunger assembly 54 with a movable finger control 59 controls the grasper 55. The irrigation/instrument assembly 52 also includes a fluid inlet 57 that can comprise a Luer-style fitting connected with a sterile tubing 56 that can terminate in a source of sterile saline or water used as an irrigation fluid. Both instruments and irrigation fluid can pass down a single internal tubing (not shown) to exit at the distal end 34.

Figure 2:
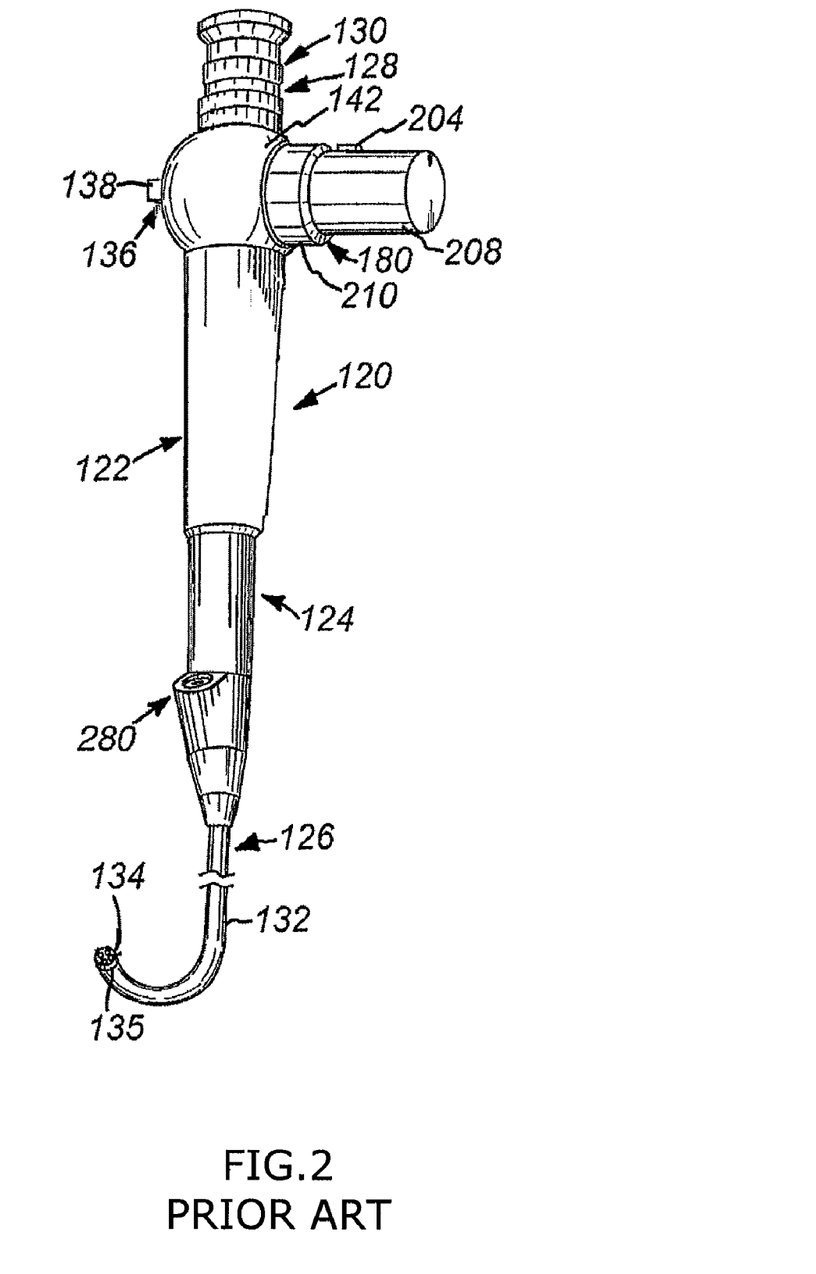
FIG. 2 is a perspective view of a prior art endoscope having an attached battery power incandescent lamp light source.

Prior attempts to produce endoscopes that are not tethered by such a fiber optic light source cable 44 to an external light source 46 have produced light sources and battery power supplies that are external to and separate from the endoscope handle, yet still use inefficient light sources, such as halogen lamps. An example of this form of prior art endoscope is illustrated by FIG. 2, which is also simplified from FIG. 2 of U.S. Pat. No. 5,630,783. This prior art endoscope 120 includes a body or housing 122 having a distal end 124 and a proximal eyepiece 128. The eyepiece 128 includes an adjustment or focus ring 130. The distal end 124 of the housing 122 supports a semi-rigid, flexible, tube 126, which is covered with a flexible, low friction, sheathing 132, and includes a distal end 134 having a polished metallic ring 135 with a series of openings. A steering control 136 including a movable steering control lever 138 is mounted on an enlarged ball section 142 of the housing 122. A fitting 280 is provided adjacent the distal portion 124 of the housing 122 for the introduction of instruments, such as graspers and biopsy forceps, medicaments and small quantities of saline or water irrigation fluids.

This prior art endoscope has a self-contained illumination source 180 attached in the position of the fiber optic light source cable connector 50 of FIG. 1. The source 180 utilizes a high intensity incandescent light bulb. The bulb can be a halogen-type bulb for greater intensity and whiter light. The battery and switch 204 are self-contained within a removable housing 208 that is joined to the upper portion of the handle 122 by a threaded ring coupling 210. The battery can be a rechargeable nickel-cadmium or equivalent battery, such as a lithium-ion battery. Other endoscopes with an add-on battery powered light sources using an incandescent halogen bulb are known, for example, at http://www.pentaxmedical.com/Products/Bronchoscopy/PortableBronch.asp.

Such add-on battery powered light sources not only are inefficient and clumsy, but the connection to the endoscope handle is an additional site for leakage, corrosion and contamination. In general, after each use in a medical procedure, the endoscope is cleaned to remove detritus, and subsequently disinfected and/or sterilized. Standard cleaning and disinfection procedures require that the entire endoscope, including the endoscope handle, is completely immersible and watertight, and leak testing is performed routinely as part of the cleaning and disinfection process. Fluids used during the disinfection process (http://www.fda.gov/cdrh/ode/germlab.html), such as activated alkaline glutaraldehyde, peracetic acid and orthophthaldehyde, are harsh and corrosive chemicals. Fluid leakage into the interior of the endoscope handle and contact with electronic circuits and components can damage both a light source and its power supply if located within the endoscope handle.

Thus, there is a need for a fully self-contained endoscope that is not tethered to an external light and/or power source and that can withstand multiple uses and cleanings while maintaining the integrity of the liquid sensitive components of the endoscope.

SUMMARY OF THE INVENTION

The present invention provides an endoscope having a shaft and a handle that are liquid and gas impermeable, having inside the handle an internal solid-state light source and a further internal sealed compartment that is liquid impermeable and gas permeable and that contains at least one battery and a light source control circuit that provides continuous control of the light intensity produced by the internal solid-state light source.

In preferred embodiments, the invention provides an endoscope having a proximal end and a distal end comprising an elongated shaft at the distal end that is connected to an endoscope handle at the proximal end of the endoscope, the endoscope handle having a proximal end and a distal end and an exterior, an interior, and a longitudinal axis, wherein the shaft and the endoscope handle are sealed to be liquid and gas impermeable; optical components located at or near the proximal end of the endoscope handle; a solid-state light source contained within the interior of the endoscope handle; and a sealed compartment contained within the interior of the endoscope handle, wherein the sealed compartment contains at least one battery that powers a light source control circuit electrically connected to the solid-state light source. Typically, the optical components include an eyepiece, a still camera or a video camera. In preferred embodiments, the eyepiece is interchangeable with a still camera or a video camera. In other embodiments, a capacitor can be used in place of a battery to store energy, and then discharged to power the light source and electronics.

In other preferred embodiments, the present invention provides an immersible endoscope having a proximal end and a distal end comprising an elongated shaft at the distal end connected to an endoscope handle at the proximal end that has a exterior and an interior, wherein the shaft and the endoscope handle are sealed to be liquid and gas impermeable; a solid-state light source contained within the interior of the endoscope handle; and a liquid impermeable and gas permeable sealed compartment that is contained within the interior of the endoscope handle, wherein the sealed compartment contains at least one battery that powers a light source control circuit electrically connected to the solid-state light source, wherein the light intensity produced by the internal solid-state light source can be continuously varied. In preferred embodiments, the solid-state light source is a light emitting diode, more preferably a high power light emitting diode. Preferably the light source control circuit includes a linear Hall-effect sensor.

In further embodiments, the immersible endoscope has a proximal end and a distal end comprising an elongated shaft at the distal end connected to an endoscope handle at the proximal end of the immersible endoscope, the endoscope handle having a proximal end and a distal end and an exterior, an interior, and a longitudinal axis, wherein the shaft and the endoscope handle are sealed to be liquid and gas impermeable; imaging components located at or near the proximal end of the endoscope handle; a solid-state light source contained within the interior of the endoscope handle; and a sealed compartment contained within the interior of the endoscope handle that is oriented transversely to the longitudinal axis of the endoscope handle, wherein the sealed compartment has at least one liquid impermeable and gas permeable vent and contains at least one rechargeable battery that powers a light source control circuit electrically connected to the light emitting diode. Typical imaging components include an eyepiece, a still camera or a video camera. Preferably, the light produced by the internal solid-state light source can be continuously varied in intensity. Typically the light source control circuits include a linear Hall-effect sensor. Optimally, the sealed compartment is at least partially surrounded by a movable structure, such as an articulation drum.

In yet further embodiments, the endoscope has an elongated shaft at the distal end connected to an endoscope handle at the proximal end of the immersible endoscope, the endoscope handle having a proximal end and a distal end and an exterior, an interior, and a longitudinal axis, wherein the shaft and the endoscope handle are sealed to be liquid and gas impermeable; imaging components located at or near the proximal end of the endoscope handle; a light emitting diode contained within the interior of the endoscope handle; and a sealed compartment contained within the interior of the endoscope handle and oriented transversely to the longitudinal axis of the endoscope handle, wherein the sealed compartment contains at least one rechargeable battery that powers a light source control circuit electrically connected to the light emitting diode. Preferably the light emitting diode is in thermal communication with an internal frame of the endoscope handle.

Generally, the shaft includes an illumination light guide having a proximal end and a distal end, the proximal end of the illumination light guide being optically connected to the solid-state light source and the distal end of the illumination light guide extends to the distal end of the shaft. Typically, the shaft includes an image guide having a proximal end and a distal end, where the proximal end of the image guide is optically connected to the optical components and the distal end of the image guide extends to the distal end of the shaft. Alternatively, in a rigid or semi-rigid endoscope, such as a laparoscope, the shaft can include imaging and relay lenses that optically transmit the image to the eyepiece or a camera. Typically, at least part of the length of the shaft is flexible, usually near the distal end of the shaft. In certain preferred embodiments, the shaft can also contain channels for the introduction of gases, liquids, or surgical tools. In certain embodiments, the image guide or relay lens system is replaced by a solid-state camera, such as a CCD or CMOS chip, at the distal end of the shaft.

The internal sealed compartment preferably includes a liquid impermeable and gas permeable vent. In preferred embodiments, the liquid impermeable and gas permeable vent comprises an expanded polytetrafluoroethylene gas permeable membrane. In preferred embodiments, the sealed compartment is at least partially surrounded by a movable structure. In certain preferred embodiments, the movable structure is an articulation drum. Typically, the sealed compartment is oriented at an angle of about 80-100 degrees, preferably about 85-95 degrees, to the longitudinal axis of the endoscope handle.

In general, the endoscope handle has a distal portion attached to the shaft, a proximal portion including an eyepiece at the proximal end of the endoscope, and a transverse portion that separates the distal portion from the proximal portion. In preferred embodiments, the transverse portion of the endoscope handle contains the sealed compartment partially enclosed by an articulation drum.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE PREFERRED EMBODIMENTS

The present invention provides an endoscope with a watertight and air-tight endoscope handle that in preferred embodiments contains in its interior a solid-state light source and a gas permeable and liquid impermeable sealed compartment holding a battery and an electronic circuit board, where the sealed compartment is preferably transverse to the long axis of the endoscope handle. In certain embodiments, the sealed compartment is at least partially surrounded by a movable structure.

The present invention provides an endoscope having a watertight and airtight endoscope handle that encloses an internal solid-state light source and power supply and a rigid or at least partially flexible shaft. In preferred embodiments, the endoscope handle has three portions: a distal portion attached to the shaft, a proximal portion including an eyepiece and imaging optics and a transverse portion that separates the distal portion from the proximal portion of the endoscope handle. In preferred embodiments, the transverse portion includes at least one articulation drum(s), and a sealed compartment that encloses a solid-state light source and a power supply for the solid-state light source that includes a battery, and electronic circuits for controlling the light intensity produced by the solid-state light source. In preferred embodiments, the solid-state light source is a light emitting diode (LED).

In preferred embodiments the LED is mounted to a heat-conducting internal frame of the endoscope handle. In certain embodiments, the heat-conducting internal frame contacts a heat-conducting exterior of the endoscope handle, thereby further dissipating heat produced by the operation of the LED. In other embodiments, the exterior of the endoscope handle is not heat conducting, providing a comfortable grip for the operator. In preferred embodiments, the battery and electronic components of the LED power source are contained within a fixed sealed compartment that is at least partially surrounded by a movable structure, such as an articulation drum.

The sealed compartment is liquid impermeable but gas permeable, preventing corrosive fluids from leaking into or out of the sealed compartment, but leaving the compartment in communication with the interior of the endoscope handle for the increase in air pressure needed for leak testing. In this way, all of the seals of the endoscope, including that of the battery compartment, can be validated by the user. Since the endoscope shaft will likely over time leak into the interior of the handle, the fluid intrusion will not reach the battery and electronics, thus avoiding corrosion of the electronics. Similarly, if the battery leaks, the leaked fluid will not contaminate the interior of the endoscope handle, nor have a path to the patient. By placing the electronics in the sealed battery compartment within the articulation drum, previously unused space is used to house the battery and the electronics, thereby minimizing the additional volume need to incorporate the solid state light source and the light source power supply.

A Hall-effect sensor in the battery compartment senses the magnetic field produced by a moveable permanent magnet located outside the sealed scope body. The linear Hall-effect sensor has a response proportional to the applied magnetic field, which then sends a control signal to the electronics, setting the LED output light level by adjusting the LED's drive current. The combination of the moveable permanent magnet and the linear Hall-effect sensor thus serve both as an ON/OFF switch and as a continuously variable light intensity control. Because the magnet is located outside the sealed endoscope handle, the seal that would be needed for a moving conventional switch is not needed. Currently, rubber boots are used to cover and seal switches, typically ON/OFF or momentary pushbutton switches. In order to produce variable light intensity, a potentiometer or rotary switch would have to be employed with a sealing mechanism (probably a rotating shaft seal incorporating an O-ring), which is a potential source of failure. This is particularly problematic when the switch has electrical power applied to it. While the articulation mechanism (rotating shaft) has a rotating seal, there is no electrical power associated with this moving part.

Figure 3:
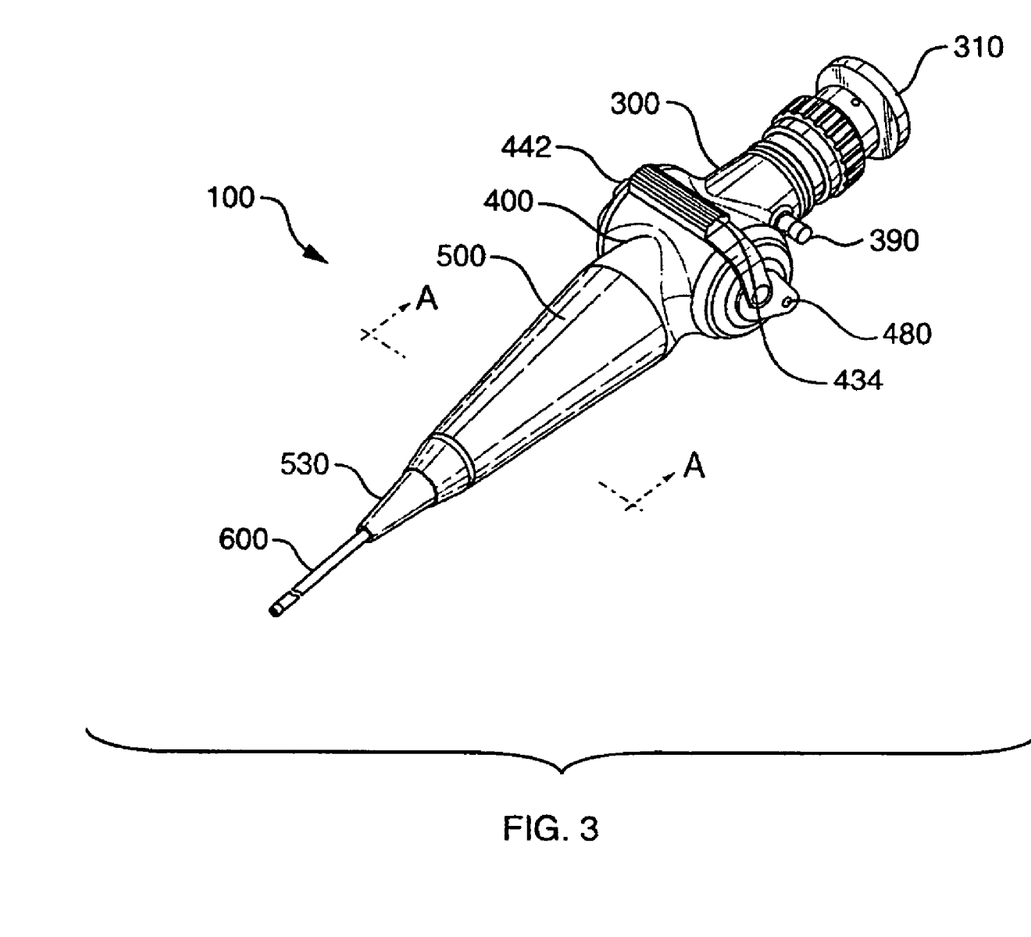
FIG. 3 is a perspective view of an embodiment of the endoscope 100 of the present invention.

As shown in FIG. 3, an embodiment of the endoscope 100 of the present invention has an eyepiece 310 at the end proximal to the user and at the opposite (distal) end is a shaft 600 that includes one or more light guides. In preferred embodiments, the proximal portion 300 and the distal portion 500 of the endoscope handle are separated by a transverse portion 400. In certain embodiments, the axis of the transverse portion 400 of the endoscope handle may be at an angle of 80-100 degrees, more preferably about 85-95 degrees to the longitudinal axis of the rest of the endoscope handle. In preferred embodiments, the axis of the transverse portion 400 of the endoscope handle is perpendicular to the longitudinal axis of the rest of the endoscope handle. The axes of the transverse portion 400 and of the rest of the endoscope handle may or may not lie in the same plane. In certain preferred embodiments, the axis of the transverse portion 400 and the longitudinal axis of the rest of the endoscope handle are approximately co-planar.

FIG. 3 also illustrates the position of leak test vent 390 in the distal portion 300 of the endoscope handle. The articulation lever 434, the magnetic illumination control lever 480, and the battery compartment cap 442 are external structures of the transverse portion 400 of the endoscope handle. The shaft boot 530 is disposed on the distal end of the endoscope handle.

Figure 4:
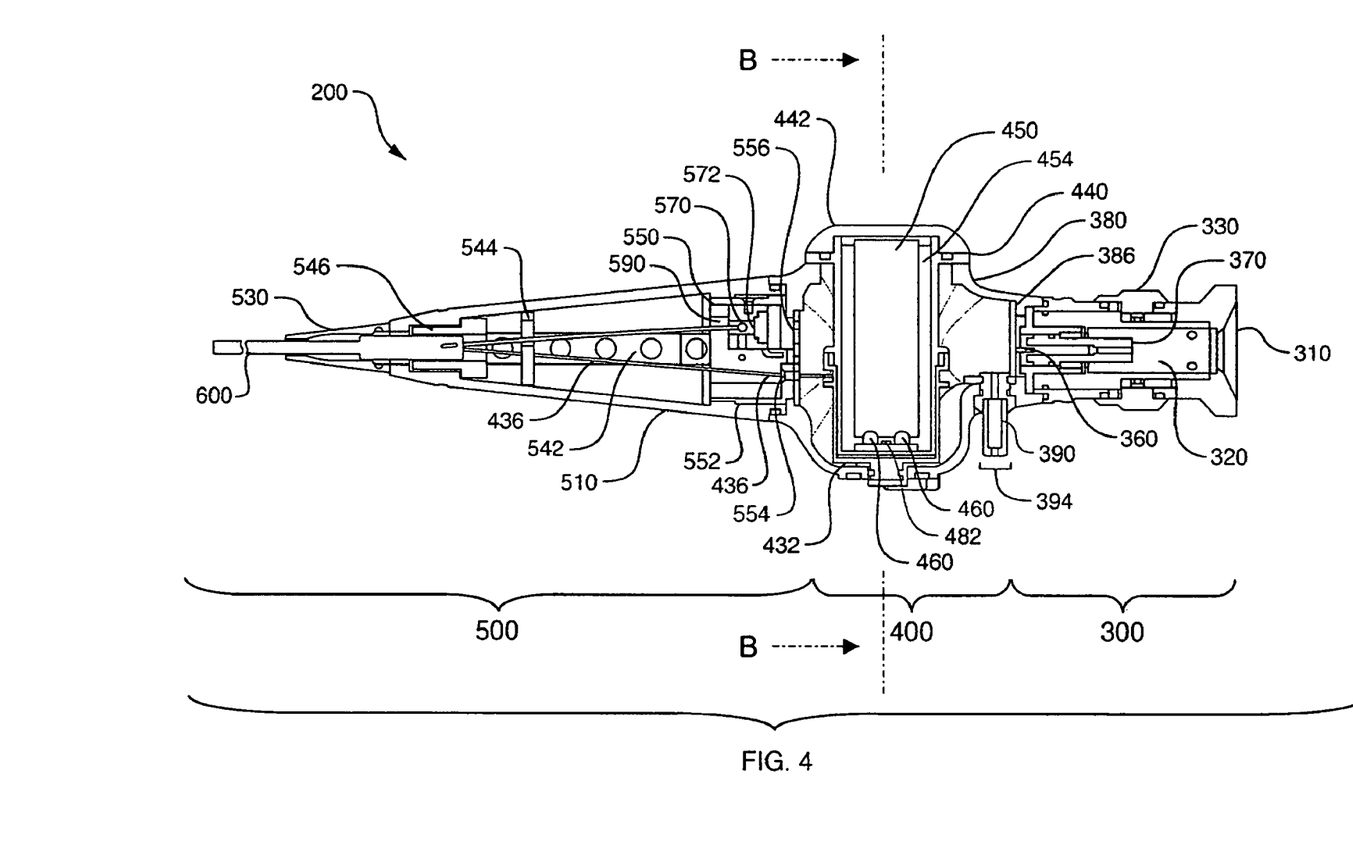
FIG. 4 is a section view through the longitudinal axis of an endoscope handle 200 in plane A-A of FIG. 3 (the plane of the leak test vent 390) of an embodiment of the endoscope of the present invention.
Figure 6:
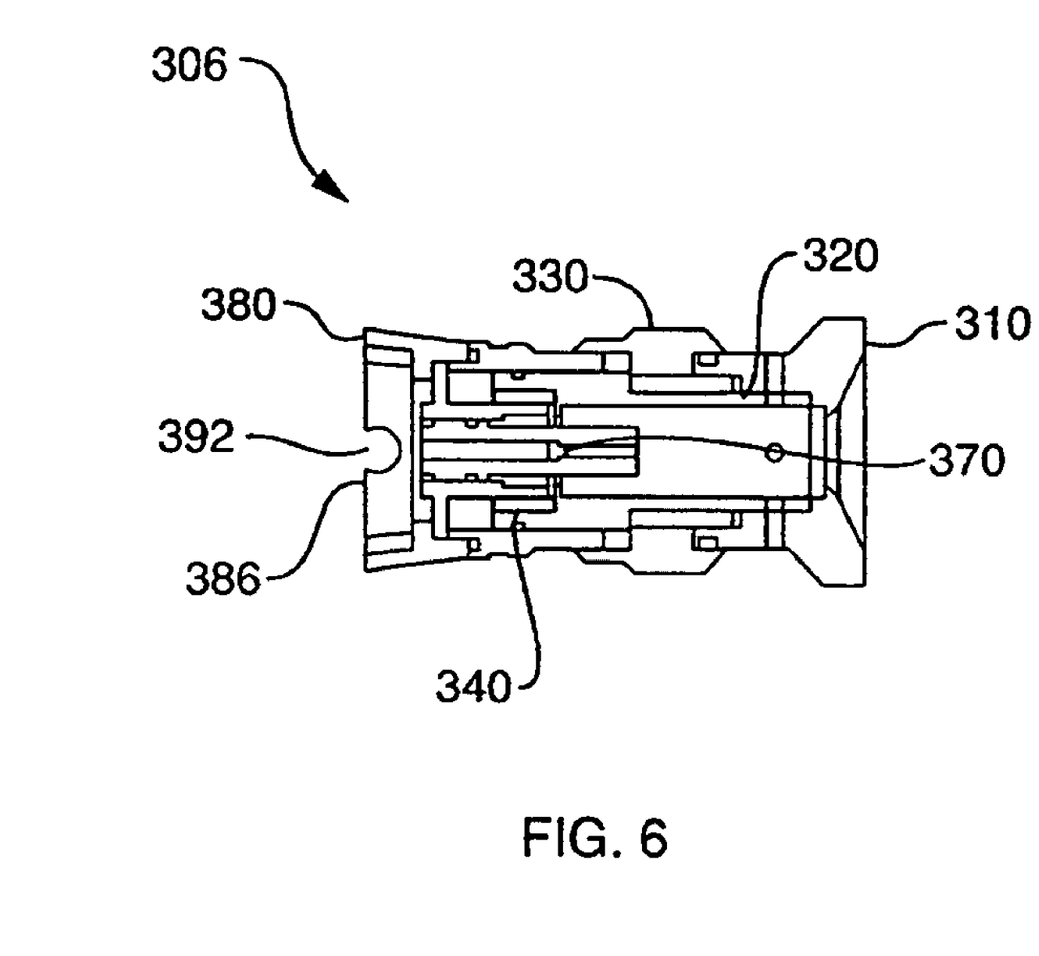
FIG. 6 is a section view through the longitudinal axis of a removable eyepiece assembly 306 of an embodiment of the endoscope of the present invention; the section is perpendicular to the plane of the section of FIG. 2.

FIG. 4 is a drawing of a section at "A-A" in FIG. 3 in a plane that passes through the longitudinal axis of an endoscope handle 200 in the plane of axis of the leak test vent 390 in an embodiment of the endoscope of the present invention. The approximate extents of the proximal portion 300, the transverse portion 400 and the distal portion 500 are indicated below the drawing. Structures of the proximal portion 300 of the endoscope handle include the eyepiece 310, the eyepiece lens assembly 320, the focusing ring 330, the image light guide 360, the image light guide tip adapter 370, body 380 of the endoscope handle 200, the backing plate 386, the leak test vent 390, and the leak test vent cap 394. An alternative embodiment of a removable eyepiece assembly is illustrated in FIG. 6.

When not in use, described below, the leak test vent 390 is normally covered, preferably with a removable cap. In preferred embodiments, the leak test vent 390 is a poppet valve. When the leak test vent 390 is a poppet valve, the leak test vent cap 394 holds the leak test vent 390 open when it is in place to aeration, shipping and ethylene oxide sterilization. Removal of the leak test vent cap 394 allows the poppet valve to close, preventing fluid invasion. In embodiments in which the leak test vent 390 is a poppet valve, the leak test vent cap 394 should be removed for patient use, leak testing, cold-soak disinfection (e.g., with a 2% glutaraldehyde solution), or disinfection using a endoscope disinfection processor, such as the STERIS SYSTEM 1® processor (STERIS Corporation, Mentor, Ohio).

Figure 5:
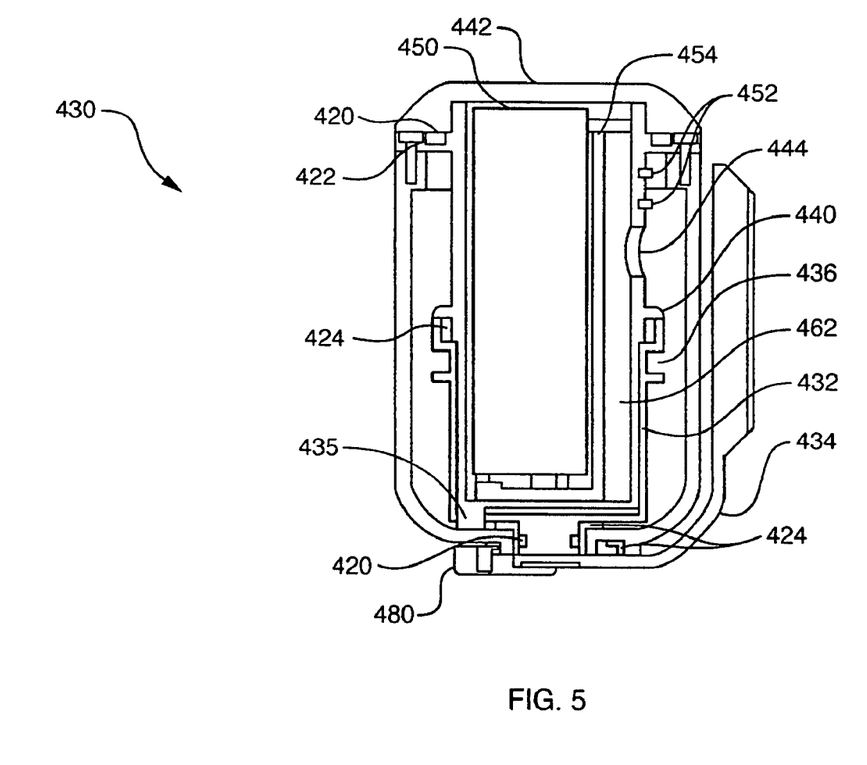
FIG. 5 is a section view through plane B-B of FIG. 2 of an articulation assembly 430 of an embodiment of the endoscope of the present invention.

FIG. 4, a section view through the transverse portion of the endoscope handle 400, shows the battery compartment 440, the battery compartment cap 442, the battery 450, and the battery chassis 454 that includes the Hall-effect sensor 482 and battery connections 460 to the light source power and control circuitry. The battery compartment 440 is disposed within the articulation drum 432, which is attached to the articulation wires 436. The articulation wires 436 pass through the distal portion 500 of the endoscope handle into the shaft 600. Rotation of the articulation drum 432 using the articulation lever 434 (see FIG. 3 and FIG. 5) takes up or pays out the articulation wires 436, providing controlled movement of the distal end of the shaft. Further details of the transverse portion 400 of the endoscope handle are shown in FIG. 5, which is a section view in the plane "B-B."

As illustrated in FIG. 4, in preferred embodiments, the distal portion 500 of the endoscope handle includes a housing 510, a subframe support beam 542 and a shaft boot 530. The subframe 540 includes a subframe base assembly 550 that is connected to at least one subframe wall 544 and a subframe tip 546 by at least one subframe support beam 542. In preferred embodiments, the subframe base assembly 550 is secured to the housing of the transverse portion 400 of the endoscope handle by the use of a backing plate 556. Alternatively, the subframe base assembly 550 may be secured directly to the housing of the transverse portion 400 of the endoscope handle. In certain preferred embodiments, the subframe base assembly 550 includes a base plate 554 and a wall 552 disposed approximately perpendicular to the base plate 554. The base plate 554 contains one or more openings to accommodate the articulation wire 436 and the image guide 360.

Figure 7A:
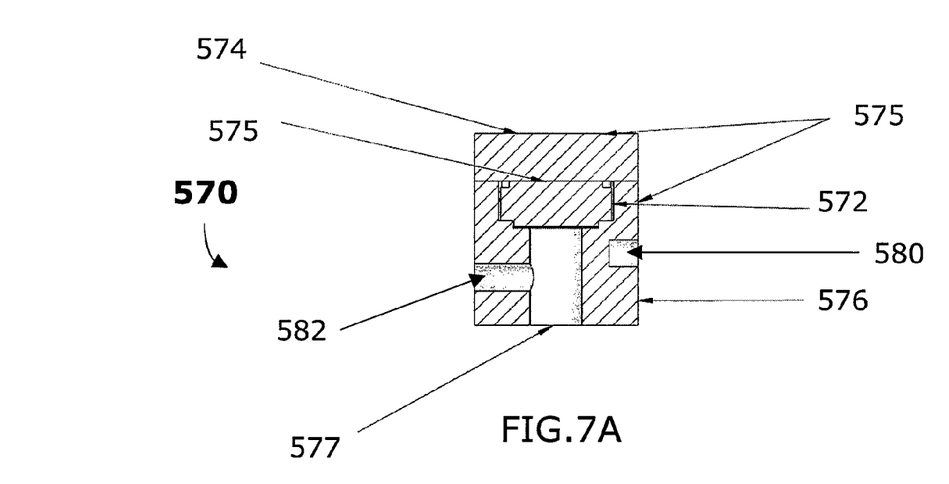
FIG. 7A is a section view through a light source assembly 570 of an embodiment of the endoscope of the present invention.
Figure 7B:
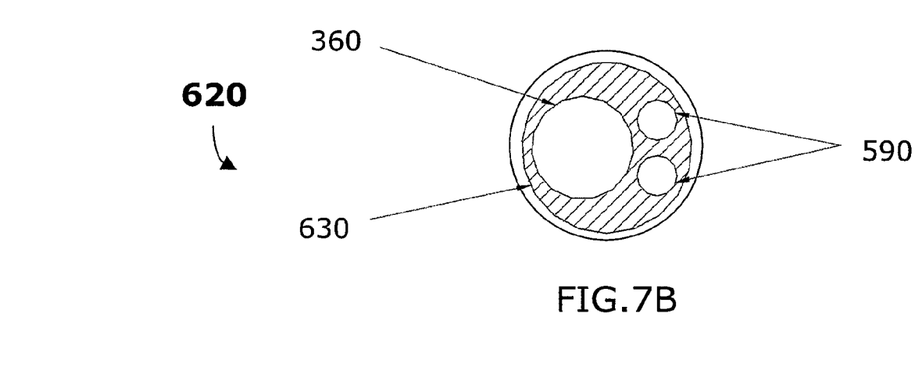
FIG. 7B is a view of the distal end 620 of the shaft 600 of an embodiment of the endoscope of the present invention.

The light source assembly 570 is preferably disposed within the subframe base assembly 550, and optimally coupled to the subframe base assembly 550 to provide a heat sink for the light source. In preferred embodiments, the light source is solid-state light source such as a light emitting diode (LED) 572 or a laser diode. The illumination light guide 590 is mounted at its proximal end, crosses the distal portion of the endoscope handle, and distally ends at the end cap of the shaft (FIG. 7B). Further details of the lights source assembly 570 are shown in FIG. 7A.

A preferred embodiment of the endoscope of the present invention uses a high power LED (Luxeon K2 Model LXK2-PWC4-0160, Lumileds Lighting, LLC, 370 W. Trimble Road, San Jose, Calif. 95131) with a typical forward voltage of 3.72V and operating current at 1000 mA. This device can be safely operated up to a current of 1.5 A with a corresponding typical forward voltage of 3.85V. This white LED has a typical color temperature of 6500K. The LED chip has an emitting surface of approximately 1 mm×1 mm, and is coated with a wavelength conversion phosphor (and/or fluorophor) that emits a broadband continuum of visible white light between about 470-700 nm. Suitable ways of coupling the light-emitting surface of such a high power LED to a light guide are disclosed in U.S. Pat. No. 7,229,201. Briefly, the dome lens of the high power LED is removed, along with the index-matching gel. The illumination light guide fiber bundle is polished flat and placed directly onto the LED (or the LED'S phosphor coating) in order to maximize the amount of light coupled into the fiber optic light guide.

Generally, the light emitting area of the LED is coupled to a small 1 mm square or round bundle of light guide fibers. This is a typical light guide bundle size used in endoscopes. The light guide bundle is typically composed of hundreds of individual glass (or plastic) fibers grouped together to form a single bundle at the light source, and either a single bundle or multiple bundles at the distal end of the endoscope. Such bundles can take on a variety of shapes at the distal end depending upon the design of the particular endoscope: one or more round bundles, a circular halo, a crescent, or the like. Small diameter fibers, typically 30-50 micrometers in diameter, are employed because these small fibers are flexible (necessary for flexible endoscopes that bend during use), or because they are required to fit into the narrow spaces around the optics either in the shaft or distal head of the endoscope.

Other types of light guides can be coupled to the LED in the manners described herein, including: liquid light guides, plastic or glass fibers, plastic or glass rods, and tapers made from fibers (glass and plastic) or solid tapers (glass and plastic). Single glass or plastic fibers may comprise the light guide. Such fibers around 1 mm in diameter are typically flexible. In order to accommodate a small light guide bundle of less than the LED emitting area, a fiber optic or solid plastic or glass taper may be placed between the LED emitting surface and the bundle, acting as an adapter that captures substantially all of the light emitted from the LED and efficiently couples it into the fiber bundle that delivers the light to the distal end of the instrument.

FIG. 5 is a drawing of a section through plane B-B of FIG. 4 of an articulation assembly 430 of an embodiment of the endoscope of the present invention. The plane B-B of section passes through the articulation lever 434 (see FIG. 1) and is roughly perpendicular to the longitudinal axis of the endoscope handle. The articulation assembly 430 is a major part of the transverse portion of the endoscope handle 400. The articulation assembly 430 includes the articulation drum 432, the articulation stop 452, and the articulation wire 436 in addition to the articulation lever 434. The battery compartment 440 is disposed within the articulation drum 432, and maintains a fixed position in the endoscope handle when the articulation drum 432 rotates around it as the shaft tip is moved. The battery compartment 440 has a gas permeable, liquid impermeable vent 444 that includes a gas permeable membrane such as an expanded polytetrafluoroethylene gas permeable membrane. Suitable expanded polytetrafluoroethylene gas permeable membranes include Gore protective vents, preferably QPE quick pressure equalization vents (W.L.Gore & Associates, Newark, DE;

http://www.gore.com/en_xx/products/venting/technical/qpe.html).

The battery compartment 440 is sealed by the battery compartment cap 442, and contains a battery 450 and the battery chassis 454. The battery chassis 454 supports the battery 450 within the battery compartment 440 and is attached to the electrical circuit board 462, which includes the light source power and control circuitry and components. The openings through the battery compartment 440 for the wires 452 connecting the electrical circuit board 462 and the LED 752 (FIG. 4 and FIG. 7A) are sealed with epoxy, silicone adhesive or other suitable adhesive after assembly. Also shown in FIG. 5 are O-ring seals 420, a gasket seal 422 and bushings 424.

The battery is a rechargeable battery, preferably a lithium ion rechargeable battery. When the solid-state light source is a high power LED, a preferred battery is the Konica Minolta NP700 lithium ion battery, 3.6V nominal voltage, 1000 mAHr typical capacity, or equivalent. This battery is used in several digital cameras and is commercially available.

In some embodiments, the battery can be charged in place in the endoscope handle, using inductive coupling to a battery charger and venting the handle through the leak test vent 390. Alternatively, the battery is charged in an external battery charger plugged into a wall outlet.

In a preferred embodiment, the Hall-effect sensor 482 (FIG. 4) is attached to the end of the battery chassis 454 that is farthest from battery compartment cap 442. The linear Hall-effect sensor 482 has an electrical response that is proportional to the applied magnetic field generated by the magnetic illumination control lever 480. A change in the position of the magnetic illumination control lever 480 produces a corresponding change in the electrical response of the linear Hall-effect sensor 482, resulting in a change in the light intensity produced by the LED. The combination of the external magnetic illumination control lever 480 and the internal linear Hall-effect sensor 482 thus provides ON/OFF switching and continuously variable light intensity control of the solid-state light source. Suitable linear Hall-effect sensors are available from Allegro MicroSystems, Worcester, Mass., such as Models A1391, A1392, A1393, and A1395. When the solid-state light source is a high power LED, a preferred linear Hall-effect sensor is Allegro MicroSystems Model A1391. In other embodiments, variable light intensity can be produced using a pushbutton switch having a suitable cover and seal, e.g., a rubber boot, wherein the amount of power applied to a LED is proportional to the length of time that the switch is held closed.

FIG. 6 is a drawing of a section through the longitudinal axis of a removable eyepiece assembly 306 of an embodiment of the endoscope of the present invention; the section is perpendicular to the plane of the section of FIG. 4. Shown are the eyepiece 310, the eyepiece lens assembly 320, the focusing ring 330, the image light guide tip adapter 370, body 380 of the endoscope handle 200, the backing plate 386 and the leak test vent mounting hole 392. The J fitting connector 340 allows the replacement of the eyepiece assembly 306 with a video camera or a single frame digital camera, avoiding the need for an optical coupler to connect the eyepiece to a digital or video camera. Alternatively, an adapter can be fitted to the eyepiece and used to couple the endoscope eyepiece to a multi-use electronic device, such as a personal digital assistant (PDA) as disclosed in published international patent application WO 2006/055949. In another embodiment, a suitable digital camera and coupler kit can be used that is commercially available from Optim, Incorporated (Sturbridge, Mass.).

FIG. 7A is a drawing of a section through a light source assembly 570 of an embodiment of the endoscope of the present invention. In preferred embodiments, a solid-state light source 572, such as a high power LED (Luxeon K2 Model LXK2-PWC4-0160, Lumileds Lighting, LLC, 370 W. Trimble Road, San Jose, Calif. 95131) is mounted on a LED backing plate 574 and placed in a LED housing 576 that is mounted in the subframe base assembly (550 in FIG. 4) using thermally conductive electrically isolating epoxy 575. The light source assembly 570 is preferably configured with at least one mounting hole 580 adapted to engage a fastener to mount the light source assembly 570 to the subframe base assembly. The light source assembly 570 preferably also includes at least one receptacle fastener hole 582 adapted to stabilize the proximal end of the illumination light guide in the illumination light guide receptacle 577. Suitable ways of coupling the light-emitting surface of such a high power LED to a light guide are disclosed in U.S. Pat. No. 7,229,201. After mechanical attachment of the light guide to the light source assembly, the light guide is sealed to the housing with epoxy, silicone adhesive or other suitable adhesive to prevent fluid intrusion.

FIG. 7B is a drawing of a view of the distal end 620 of the shaft 600 of an embodiment of the endoscope of the present invention, showing the distal end of the image light guide 360 and the distal end(s) of at least one illumination light guide(s) 590.

LEAK TESTING

The endoscope is tested to ensure that there are no leaks before high-level disinfection using a disinfectant such as a 2% glutaraldehyde solution or peracetic acid, or sterilization using ethylene oxide (EtO). The leak test vent cap 394 is removed from the leak test vent 390 and a leak tester is attached to the leak test vent. Suitable leak testers are commercially available, for example from Optim Incorporated (Part No. 004918) or from Surgical Repairs International (Tonawanda, N.Y., http://www.srirepairs.com/products_leaktesters.asp). Using the leak tester, the interior of the endoscope is pressurized to about 140-180 mmHg as measured on the leak tester. The pressure measurement is observed for about 10 seconds to determine if the connection between the leak tester and the leak test vent is loose. If the pressure drops, the connection between the endoscope leak test vent and the leak tester may be loose. The attachment and pressurization procedure is repeated to verify the connection. If the pressure drops again, the endoscope may have a damaged seal and should not be immersed in any liquid. The endoscope should be repaired prior to use or cleaning.

If the pressure does not drop, the entire endoscope, while pressurized, is immersed in water. The endoscope is observed for about 30 seconds. The distal end of the shaft is articulated up and down during this period; since holes in the soft covering of the distal end of the shaft may not be evident in a relaxed position. In addition, the battery cap seal should also be inspected during this period for leaks, since the interior of the battery chamber becomes pressurized through the gas permeable, liquid impermeable vent. A continuous stream of bubbles indicates a leak. The endoscope should be kept under pressure while removing it from the water to avoid corrosion caused by infiltration of the water into the leak site.

Typically, the leak test should be performed right after using the scope to ensure there are no leaks prior to immersing the scope in disinfection liquid. It would be wise to check the scope for leaks after replacing the battery before use. If the seal is compromised leak testing will prevent contamination of the battery and its compartment within the scope by the entry of any patient fluid or debris.

The claims should not be read as limited to the described order or elements unless stated to that effect. Therefore, all embodiments that come within the scope and spirit of the following claims and equivalents thereto are claimed as the invention.

What is claimed:

1. An endoscope having a proximal end and a distal end comprising:
    an elongated shaft having a proximal end and a distal end disposed at the distal end of the endoscope connected to
    an endoscope handle that is disposed at the proximal end of the endoscope,
    the endoscope handle having a proximal end and a distal end and an exterior, an interior, and a longitudinal axis, wherein the shaft and the endoscope handle are sealed to be liquid and gas impermeable;
    optical components located at or near the proximal end of the endoscope handle;
    a solid-state light source contained within the interior of the endoscope handle; and
    a sealed compartment contained within the interior of the endoscope handle, wherein the sealed compartment contains at least one battery that powers a light source control circuit electrically connected to the solid-state light source;
    wherein the sealed compartment comprises a liquid impermeable and gas permeable vent;
    the liquid impermeable and gas permeable vent of the sealed compartment comprises a liquid impermeable and qas permeable membrane, the liquid impermeable and qas permeable membrane being configured to provide gaseous communication between components contained by the sealed compartment and the interior of the endoscope handle; and
    a leak test vent carried by the endoscope handle, the leak test vent configured to direct gas to the interior of the endoscope handle and to an interior of the sealed compartment via the liquid impermeable and gas permeable membrane of the sealed compartment.

2. The endoscope of claim 1 wherein the sealed compartment is oriented at an angle of about 80-100degrees to the longitudinal axis of the endoscope handle.

3. The endoscope of claim 1 wherein the optical components include an eyepiece, a still camera or a video camera.

4. The endoscope of claim 3 wherein the eyepiece is interchangeable with a still camera or a video camera.

5. The endoscope of claim 1 wherein the light produced by the internal solid-state light source can be continuously varied in intensity.

6. The endoscope of claim 1 wherein the internal solid-state light source is a light emitting diode.

7. The endoscope of claim 1 wherein the shaft further comprises an illumination light guide having a proximal end and a distal end, wherein the proximal end of the illumination light guide is optically connected to the solid-state light source and the distal end of the illumination light guide extends to the distal end of the shaft.

8. The endoscope of claim 1 wherein the shaft further comprises an image guide having a proximal end and a distal end, wherein the proximal end of the image guide is optically connected to the optical components and the distal end of the image guide extends to the distal end of the shaft.

9. The endoscope of claim 1 wherein at least part of the shaft is flexible.

10. The endoscope of claim 1 wherein the sealed compartment is at least partially surrounded by a movable structure.

11. The endoscope of claim 10 wherein the movable structure is an articulation drum.

12. The endoscope of claim 1 wherein the light source control circuit includes a linear Hall-effect sensor.

13. The endoscope of claim 1 wherein the battery is a rechargeable lithium ion battery.

14. The endoscope of claim 13 wherein the battery is recharged by inductive coupling to a battery charger.

15. An immersible endoscope having a proximal end and a distal end comprising:
    an elongated shaft at the distal end connected to
    an endoscope handle at the proximal end of the immersible endoscope, the endoscope handle having a proximal end and a distal end and an exterior, an interior, and a longitudinal axis, wherein the shaft and the endoscope handle are sealed to be liquid and gas impermeable;
    imaging components located at or near the proximal end of the endoscope handle;
    a solid-state light source contained within the interior of the endoscope handle; and
    a sealed compartment contained within the interior of the endoscope handle that is oriented transversely to the longitudinal axis of the endoscope handle, wherein the sealed compartment has at least one liquid impermeable and gas permeable vent and contains at least one rechargeable battery that powers a light source control circuit electrically connected to the light emitting diode;
    the liquid impermeable and qas permeable vent of the sealed compartment comprises a liquid impermeable and gas permeable membrane, the liquid impermeable and qas permeable membrane being configured to provide gaseous communication between components contained by the sealed compartment and the interior of the endoscope handle; and
    a leak test vent carried by the endoscope handle, the leak test vent configured to direct gas to the interior of the endoscope handle and to an interior of the sealed compartment via the liquid impermeable and gas permeable membrane of the sealed compartment.

16. The endoscope of claim 15 wherein the imaging components include an eyepiece, a still camera or a video camera.

17. The endoscope of claim 15 wherein the light produced by the internal solid-state light source can be continuously varied in intensity.

18. The endoscope of claim 15 wherein the internal solid-state light source is a light emitting diode.

19. The endoscope of claim 18 wherein the light emitting diode is in thermal communication with an internal frame of the endoscope handle.

20. The endoscope of claim 15 wherein the sealed compartment is at least partially surrounded by a movable structure.

21. The endoscope of claim 15 wherein the light source control circuit includes a linear Hall-effect sensor.

22. An immersible endoscope having a proximal end and a distal end comprising:
    an elongated shaft at the distal end connected to
    an endoscope handle at the proximal end of the immersible endoscope, the endoscope handle having a proximal end and a distal end and an exterior, an interior, and a longitudinal axis, wherein the shaft and the endoscope handle are sealed to be liquid and gas impermeable;
    imaging components located at or near the proximal end of the endoscope handle;

a light emitting diode contained within the interior of the endoscope handle; and a sealed compartment contained within the interior of the endoscope handle and oriented transversely to the longitudinal axis of the endoscope handle, wherein the sealed compartment contains at least one rechargeable battery that powers a light source control circuit electrically connected to the light emitting diode, wherein the sealed compartment comprises a liquid impermeable and gas permeable vent;

the liquid impermeable and gas permeable vent of the sealed compartment comprises a liquid impermeable and gas permeable membrane, the liquid impermeable and gas permeable membrane being configured to provide gaseous communication between components contained by the sealed compartment and the interior of the endoscope handle; and a leak test vent carried by the endoscope handle, the leak test vent configured to direct gas to the interior of the endoscope handle and to an interior of the sealed compartment via the liquid impermeable and gas permeable membrane of the sealed compartment.

23. The endoscope of claim 22 wherein the sealed compartment is at least partially surrounded by a movable structure.

24. The endoscope of claim 22 wherein the light source control circuit includes a linear Hall-effect sensor.

* * * * *